United States Patent [19]

Hirdes

[11] 3,990,152
[45] Nov. 9, 1976

[54] DENTAL APPLIANCE FOR INTRODUCING A FILLER MATERIAL INTO A TOOTH CAVITY

[76] Inventor: Rüdiger Hirdes, Tippelsberger Str. 42, D - 4630 Bochum, Germany

[22] Filed: Dec. 23, 1974

[21] Appl. No.: 535,312

[30] Foreign Application Priority Data
Dec. 24, 1973  Germany............................ 2364547

[52] U.S. Cl.................................. 32/60; 222/252; 222/333
[51] Int. Cl.$^2$........................................... A61C 5/04
[58] Field of Search .............. 32/60, 40 A; 222/252, 222/253, 263, 325, 333, 340, 254

[56] References Cited
UNITED STATES PATENTS

| | | | |
|---|---|---|---|
| 3,088,207 | 5/1963 | Borsuk................................... | 32/60 |
| 3,221,409 | 12/1965 | Thiel et al............................. | 32/60 |
| 3,252,624 | 5/1966 | Watson, Jr..................... | 222/340 X |
| 3,322,307 | 5/1967 | Fraser.................................. | 32/60 X |
| 3,623,224 | 11/1971 | Smith..................................... | 32/60 |
| 3,638,314 | 2/1972 | Lopey et al............................. | 32/60 |
| 3,735,492 | 5/1973 | Karter et al............................ | 32/60 |
| 3,751,807 | 8/1973 | Noll et al............................... | 32/60 |
| 3,792,530 | 2/1974 | Smith..................................... | 32/60 |
| 3,816,922 | 6/1974 | Thiel et al............................. | 32/60 |

*Primary Examiner*—Robert Peshock
*Assistant Examiner*—Jack Q. Lever
*Attorney, Agent, or Firm*—Michael J. Striker

[57] ABSTRACT

The appliance has a support which carries a discharge nipple having an elongated interior channel formed with an inlet and an outlet. A pair of tubular guides form a first and a second passage, respectively. The first passage has an open end and the second passage communicates with the inlet of the interior channel. A replaceable magazine has an elongated chamber for a quantity of the filler material and communicates of the open end of the channel in direction transversely to the elongation of the latter. A first expelling element is reciprocable in the first passage and the chamber for expelling a portion of the chamber material and charging it into the channel. A second expelling element is reciprocable in the second passage and channel for expelling the charged portion through the outlet of the nipple. A single drive is provided which effects coordinated reciprocation of both of the expelling elements.

34 Claims, 13 Drawing Figures

DENTAL APPLIANCE FOR INTRODUCING A FILLER MATERIAL INTO A TOOTH CAVITY

BACKGROUND OF THE INVENTION

The present invention relates generally to dental appliances, and in particular to a dental appliance for introducing a filler material into a tooth cavity.

Tooth cavities are filled with various filler materials, for example amalgam. Heretofore, the dental appliances used for introducing such filler materials into the tooth cavity are of two basic types, namely one type which permits only the introduction of a quantity of the filler material into the cavity, and another type which permits only the tamping down of the introduced filler material. As every dental patient knows, this has always involved the constant exchange of one type of appliance for another as the dentist first introduces a quantity of filler material into the cavity with one appliance and then uses the other appliance to tamp it down before he can introduce an additional quantity of filler material.

The tamping appliances usually have a ball-shaped cylindrical or conical working end which is introduced into the tooth cavity to tamp down the filler material. These appliances have not undergone any significant developments in the recent past.

The manner in which the quantities of filler material are supplied, however, has in the last few years been undergoing some changes. Conventionally, the filler material is applied by a dental aide to a small carrier which is held with one hand whereas the filler material is placed onto the carrier with the other hand. This requires quite considerable skill, and even when the filler material is correctly applied to the carrier it occurs frequently that as the carrier is being handed over to the dentist for his use it may be jogged so that the quantity of filler material placed onto it will drop off and become unusable. This evidently results in losses both of time and material.

Recognizing this problem, the prior art has attempted to provide devices to overcome it. However, these devices have all failed to take into account the particular characteristics and requirements of the filler material and therefore have not been able to fulfill their intended purpose.

To properly understand the problems involved it is necessary to keep in mind that the most widely used filler material is a silver-tin amalgam. The National Bureau of Standards, the American Dental Association and the Federation Dentaire Internationaux recommend that this amalgam be composed of 65% silver, 25% tin, 6% copper, 2% zinc, 3% mercury and traces of gold and platinum. The relatively high silver content imparts to the amalgam a considerable hardness, a low flow characteristic and a rapid setting time, whereas tin reduces expansion of the material and delays the setting. The period during which the amalgam remains plastic so that it can be worked is approximately 5–10 minutes; the time required for complete hardening is approximately 2 hours. It follows that this type of amalgam which, as mentioned above, is the most widely used today, must be introduced into an applicator appliance, ejected from the same into the tooth cavity and compacted or condensed therein, all within a period of substantially 5–10 minutes while it is still plastic.

The term condensing or compacting of the amalgam refers to the ability of material to compact under the application of exterior pressure, leading to expulsion of air inclusions and of excess mercury. It is accepted dental practice that small quantities of amalgam are successively and rapidly applied to the tooth cavity and that they are tamped in order to first fill the retentions, corners and angles of the cavity, and to become compacted therein.

As pointed out before, the prior-art appliances which were developed for delivering quantities of amalgam into a tooth cavity do not take into account the particular characteristics of this filler material, and are therefore not usable.

It is known to provide a telescopically collapsible spiral spring which serves as a magazine for a quantity of the amalgam and also as a part of the expeller of the device. This spring has a tapering interior cross section and can be filled via a removable cap. The cross section of the inlet that is closed by the cap decreases drastically from the point where the inlet communicates with the expeller of the device to the outlet opening of the inlet nipple. Experience has shown that this prior-art device cannot be used with amalgam because the latter is a compressible medium due to the air inclusions that are present in it, so that a strong compression of the material, which leads to expulsion of excess mercury, results in a very rapid hardening of the amalgam. In the aforementioned prior-art device the material is subjected to such a strong compression and therefore tends to harden in and clog the device.

Furthermore, it is accepted dental practice to initially supply small quantities of amalgam into a tooth cavity, to be able to completely fill all crevices and angles of the cavity while obtaining good compacting, and only thereafter to supply larger quantities to fill the remainder of the cavity. The aforementioned device of the prior art operates precisely in the reverse manner, in that during the initial operation it supplies a large amount of amalgam and during successive operations it supplies smaller and smaller amounts as the amalgam begins to harden within the device.

Still another problem with this prior-art construction is the fact that its operation requires considerable skill, and that when it must be refilled with more amalgam the dentist must pass it on to an aide. In the meantime, that is while the device is cleaned out and refilled, the dentist must either interrupt the filling of the cavity or he must have a second already filled device available if he is to be able to continue the filling operation. The refilling of the device is time-consuming, especially taken in conjunction with the necessith to clean out the hardened amalgam from the previous charge, and it will be remembered that only between 5 and 10 minutes are available from the time the amalgam is prepared to the time at which it hardens and is no longer sufficiently plastic to be worked.

A further prior-art device has a tubular member which is fixedly mounted in the device and into which the body of amalgam to be dispensed must be introduced. This can be done only after the head of the device is previously removed in order to gain access to the tubular member, and this is time-consuming and of course faces the dentist with the necessity of either having to wait until the device is refilled or having to have a second identical device available that has already been previously filled so that he can continue the introduction of the amalgam into the tooth cavity. This device also has been found to be highly susceptible to malfunctions and has a relatively large working head which is disadvantageous because it requires more space than the distance of approximately 12–15 millimeters that is usually available between the rows of upper and lower teeth.

Still another prior-art device provides two plungers, one for dispensing amalgam from a magazine, and one for expelling the amalgam out of the device and into the tooth cavity. Each of the plungers must be manually operated against the force of a biasing spring. Experience has shown that this device is at best usable for dispensing of amalgam, but cannot be used for tamping the amalgam down in the tooth cavity, because for this purpose the dentist must exert with the index finger of his hand a pressure upon the front end of the device and must simultaneously maintain with his wrist the expelling plunger in forward position against the restoring force of the biasing spring. The magazine in this device is a single-use receptacle of rectangular interior cross-section which conically converges. This has the disadvantage that during the expulsion by the plunger a portion of the amalgam and of the mercury content thereof can enter behind the plunger into the free space created behind the plunger as the latter moves forwardly, so that it is subsequently difficult or entirely impossible to retract the plunger out of the container in order to be able to remove the same and replace it with a new one.

Another prior-art device has a guide channel formed with a slidable member that carries at its front end a piston, and another guide channel carrying in its interior a further slidable member that also carries a piston. One of the pistons serves to expel material from a container and the other serves to expel the material out of the device and into a tooth cavity. Both of the slidable members are biased by springs that act upon their trailing ends. One of the springs serves to maintain the piston of the expelling member within the interior of a bore until a slider is moved manually forwardly. The spring acting upon the other slideable member serves to continuously press filler material from a second channel that acts as a container into the upper hollow space of a discharge nipple. The trailing end of the expelling plunger is provided with a gear which is in engagement with a rack provided at the trailing end of the plunger that pushes material out of the reservoir.

This device is manually operated and the movement of the slider has to be carried out counter to the force of at least one spring. This not only requires the exertion of a considerable amount of force but also requires substantial skill in order to be able to rapidly fill a tooth cavity. Since the spring which acts upon the plunger that expels material from the reservoir loses its prestress as the reservoir becomes increasingly emptied of material, the amalgam portions that are expelled from the reservoir decrease successively. The original prestress of the spring acting upon the plunger for the reservoir must be relatively great, and this means that the slider must be shifted against a relatively high biasing force due to the meshing of the teeth on the gear and the rack. Moreover, this prior-art device has the further disadvantage that when the reservoir must be refilled the dentist must return the device to his aide, since the reservoir is fixedly mounted in the device and cannot be removed. He must then wait until the reservoir has been refilled or else he must have a second already filled device available for his use. This is of course time-consuming and cumbersome, especially in applications where a plurality of cavities are to be filled during a single appointment and where the working area must be repeatedly dried of saliva, etc.

Finally, another device is known from the prior art which essentially uses a double-acting pneumatic piston having a piston rod which is coupled via a bolt with a curved cam one end of which engages by means of a bifurcated member a transverse bolt of a filling pin. By alternatingly supplying air to the opposite sides of the double-acting piston the filling pin is moved up and down and pushes amalgam portions out of a reservoir that extends transversely to its movement, to expel them via a tubular nipple into the tooth cavity. In this construction, also, the reservoir piston is biased by a biasing spring which is prestressed and whose prestress continuously decreases as the reservoir empties of filler material. This means that during successive operations of the device amalgam portions of different amounts and in differentially pre-compacted condition are pushed by the reservoir piston into the path of movement of the filling pin. This device is not suitable for compacting the amalgam that has been introduced into the tooth cavity, and when the reservoir is to be refilled this is a rather time-consuming operation. A cleaning of the reservoir prior to refilling is absolutely essential, because otherwise the old residue of amalgam will harden and block the reservoir piston against movement so that it can no longer supply quantities of amalgam into the path of movement of the filling pin. Furthermore, the filling pin is not protected against pivoting in counterclockwise direction when it reaches its upper end position, so that the entire mechanism may become clogged and inoperative.

SUMMARY OF THE INVENTION

Accordingly, it is a general object of this invention to overcome the disadvantages of the prior art.

More particularly, it is an object of the invention to provide an improved dental appliance for introducing a filler material into a tooth cavity, which appliance avoids these disadvantages.

An additional object is to provide such an appliance which assures a rapid feeding of filler material into a tooth cavity.

A further object of the invention is to provide such an appliance which is highly reliable in operation and largely maintenance-free.

An additional object of the invention is to provide an appliance of the type in question which will supply small and constant quantities of the filler material in rapid succession, independently of the skill of manipulation of the user, and wherein the physical characteristics of the successive supplied quantities of filler material will be constant.

An additional object of the invention is to provide such a dental appliance which also serves to compact the quantities of filler material that have been introduced into a cavity.

In keeping with these objects, and with others which will become apparent hereafter, one feature of the invention resides in a dental appliance for introducing a filler material into a tooth cavity. The dental appliance comprises, briefly stated, a support, a discharge nipple on the support and having an elongated interior channel formed with an inlet and an outlet, first means forming a first passage having an open end, and second means forming a second passage which communicates with the inlet. A replaceable magazine is provided on the support and has an elongated chamber for a quantity of the filler material; this chamber communicates with the open end of the first passage and also with the channel in the nipple, in the direction transverse to the elongation of the channel. A first expelling element is reciprocable in the first passage and chamber for expelling a portion of the filler material and charging it into the channel, and a second expeller element is reciprocable in the second passage and channel for expelling this portion through the outlet of the discharge nipple. A single drive means is provided for effecting coordinated reciprocation of both of the expelling elements.

The drive means may either be a mechanical drive or a pneumatic drive.

The appliance according to the present invention assures that during each working stroke of the first expelling element a small quantity of the filler material is expelled from the replaceable magazine and charged into the interior channel of the discharge nipple, to be subsequently expelled from the discharge nipple and into a tooth cavity during the working stroke of the second expelling element. The working stroke of the second expelling element brings the leading end of the latter to a position where it closes the outlet of the discharge nipple so that the latter can be used to compact the quantity of filler material that has just been discharged and introduced into the tooth cavity. Thus, the discharge nipple works as a compacting or condensing device at this time. The fact that the magazine is replaceable means that when it has been emptied of filler material it can within seconds be replaced with a new magazine containing fresh filler material, so that no time is lost during the filling operation. While material is being discharged from the magazine in the appliance, the dental aide can refill an empty magazine in preparation for the coming exchange of magazines.

A further advantage of the appliance according to the present invention is that due to the rapid expulsion of small quantities of filler material a substantially better compacting of the material in the tooth cavity is obtained than what is possible with the prior art, and this in turn results in an improvement in the structural characteristics of the inserted filling and in a better engagement of the filler material with the walls of the tooth cavity, so that a filling produced with the appliance according to the present invention has an improved lifetime due to the excellent compacting that can be obtained as each small quantity of filler material is compacted individually. Moreover, the appliance according to the present invention makes it possible to fill a plurality of cavities during a single appointment, in succession and without requiring repeated drying of the work area, under hygienic conditions and in a fraction of the time required by the use of prior-art devices.

The working stroke of the second expelling element cannot be longer than approximately 12–15 millimeters, because the nipple and any portion of the appliance that is inserted into the mouth of a patient cannot have a greater length than this dimension because of the limited spaced availble between the upper and lower teeth. This means that due to this short working stroke the expulsion of filler material and the subsequent tamping and compacting are carried out in rapid succession, and the speed of operation can be adjusted by an appropriate adjustment to the drive means within the tolerance limits of the patient.

Due to the continuous advancement of the first expelling element which expels material from the magazine, which will be described subsequently, the filler material in the magazine is subjected to a constant pressure so that the quantities of filler material that are expelled into the interior channnel of the discharge nipple and from there into the tooth cavity all are pre-compacted to the identical extent.

According to one advantageous embodiment of the invention, the single drive means may utilize a mechanical drive that is powered by an electric motor, so that the appliance according to the present invention can be used completely independently of any other technical equipment that is available to the dentist, since the electric motor may evidently be either battery powered or line powered.

The single drive means may, however, also be a pneumatically powered drive means. The advantage of this is that most if not all dentist offices have an air-compressor available for operation of other equipment, such as drills or the like, so that the applicance can be connected to and powered by this air compressor in a simple manner. Moreover, a pneumatic drive is largely maintenance-free.

The novel features which are considered as characteristic for the invention are set forth in particular in the appended claims. The invention itself, however, both as to its construction and its method of operation, togehter with additional objects and advantages thereof, will be best understood from the following description of specific embodiments when read in connection with the accompanying drawings.

DESCRIPTION OF THE PREFERRED EMBODIMENTS

In all Figures of the drawing reference numeral 1 identifies an expelling element by means of which quantities of a filler material, such as amalgam, are expelled from the appliance of the present invention into a tooth cavity. Referene numeral 1' identifies a passage of a conduit in which the expelling element 1 is reciprocable. Reference numeral 2 identifies a further expelling element which serves to expel filler material from a replaceable magazine 3, and reference numeral 2' identifies the guide passage for the expelling element 2. Reference numeral 4 identifies a discharge nipple which is elongated and has an elongated interior channel. In the illustrated embodiments the expelling elements 1 and 2 are located in a common plane, which is the plane of FIGS. 1, 4, 6, 7, 8, 9 and 10. Each of the expelling elements 1, 2 is of a corrosion-resistant sterilizable wire of metallic or synthetic plastic material, for example steel or tetrafluoroethylene. The magazine in the exemplary embodiments is in form of a circular cylindrical sleeve having conical ends 3', 3" which are releasably receivable in engagement with cooperating surfaces on the nipple 4 and a member which is associated with the support (i.e. housing) of the appliance, as will be discussed subsequently. It is particularly advantageous if the expelling elements 1 and 2, and also the magazine 3, are of a synthetic plastic material having a high temperature resistance, such as the aforementioned polytetrafluoroethylene, or a halogenated polyethylene, particularly a polytrifluoroethylene, or a polyvenyl carbazole, a polyacrylic nitrile, a phenol formaldehyde resin, a silicon resin, a chlorided polyester or a higher polyolefin, such as for example a polypropylene, a polyvinylidenechloride or a polyisobutylene.

The dab of filler material which is to be expelled from the magazine 3 during each working stroke of the appliance, and which enters the interior channel of the nipple 4, has dimensions corresponding approximately to the dimension $h$ of the magazine outlet opening $3'''$ and the inner diameter $d$ of the interior channel in the nipple 4. It should be understood that the cross-sectional configuration of the interior $3^{IV}$ of the magazine 3 may be circular, elliptical or right-angular, as long as it is assured that this cross-sectional configuration is constant over the entire length of the magazine 3, that is the length of the magazine in the direction of movement of the expelling element 2, so that as the expelling element 2 travels through the magazine no residual amalgam or other filler material will be able to adhere to the walls of the interior of the magazine.

The end portion 3' of the magazine 3 which faces away from the nipple 4 engages a member 6 which is guided coaxially with respect to the tubular member having the passage 2' for the expelling element 2, and which is slidable against the force of a biasing spring 5. The member 6 and the spring 5 are accommodated in a sleeve 7 which is provided with an arresting pin 8 that on the one hand predetermines the prestress of the spring 5 and on the other hand guides the member 6 by extending into a groove 6' thereof. To remove one magazine 3 and replace it with a new one it is merely necessary to push the magazine 3 in against the force of the spring 5, that is in FIG. 1 to exert downward force on the magazine 3 and cause the member 6 to slide downwardly, whereupon the end portion 3" of the magazine is pivoted out of engagement with its eat on the nipple 4 so that the end portion 3' can then be moved out of engagement with its seat on the member 6. The insertion of a new magazine takes place in the reverse order. It is important to remember that the expelling element 2 must be retracted from the interior $3^{IV}$ of the magazine 3 during the removal and insertion of magazines.

Figures 1, 2:
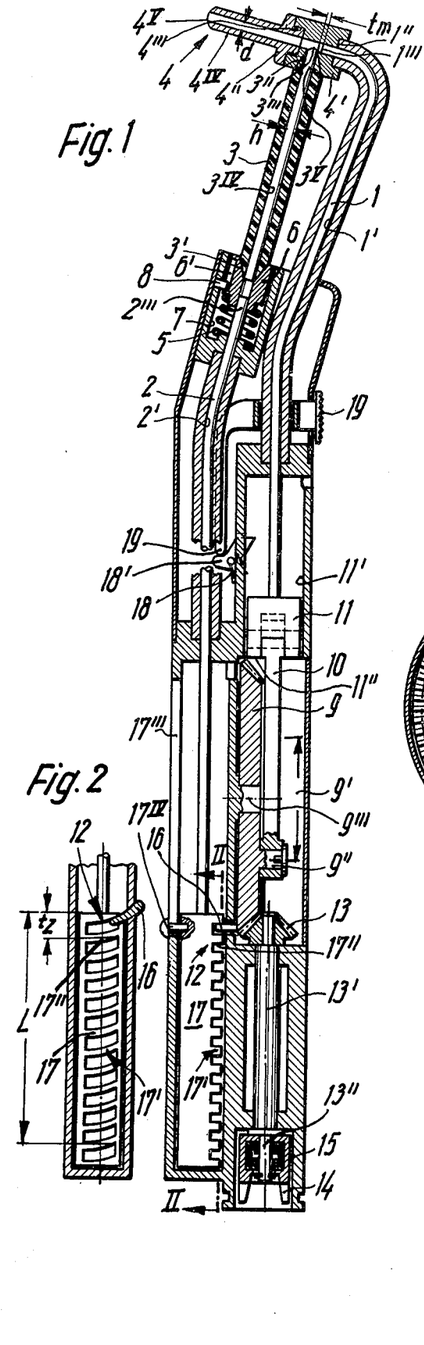
FIG. 1 is an axial section through one embodiment of my novel dental appliance, having a mechanical drive means.
FIG. 2 is a fragmentary section on line II—II of FIG. 1.
Figure 11:
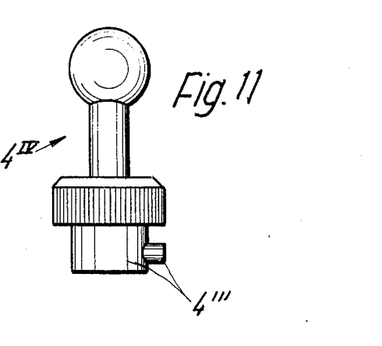
FIG. 11 is a fragmentary detail view, showing a detail of one type of discharge nipple that can be used in any of the preceding devices.
Figure 12:
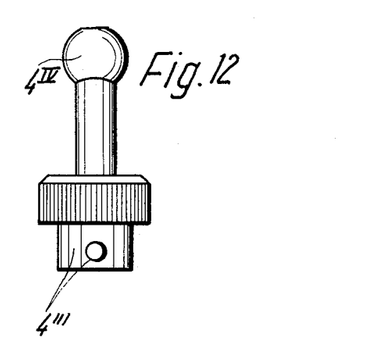
FIG. 12 is a view similar to FIG. 11, illustrating a further embodiment of a discharge nipple that can be used with any of the embodiments in FIGS. 1–10.
Figure 13:
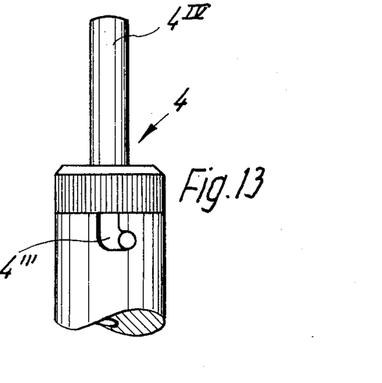
FIG. 13 is a view analogous to FIG. 12, illustrating still another embodiment of a discharge nipple that can also be used with any of the devices in FIGS. 1–10.

The discharge nipple 4 has an arresting portion 4' that is firmly connected with the end 1" of the tubular member having the guide passage 1', and a compacting sleeve portion $4^{IV}$ which can be connected with the other end 4" of the portion 4' by means of a screw connection or a bayonet connection $4''''$ (see particularly FIG. 1). The sleeve portion $4^{IV}$ may be of any of the types illustrated in FIGS. 11–13, that is, in dependence upon the size and character of the tooth cavity to be filled it may have a larger substantially spherical end portion (FIG. 11), a smaller substantially spherical end portion (FIG. 12) or a cylindrical or conical end portion (FIG. 13). Such sleeve portions $4^{IV}$ may of course be exchanged one for the other during a single cavity-filling operation, if and as required.

Figure 3:
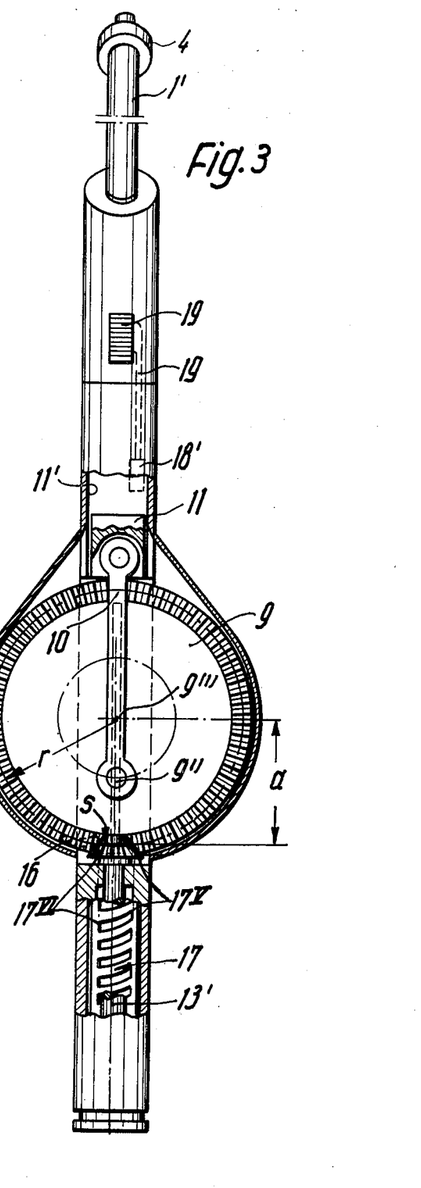
FIG. 3 is a partly sectioned side view of FIG. 1, looking towards the left.

In the embodiment illustrated in FIGS. 1–3 the dental appliance according to the present invention utilizes a single mechanical drive means which couples the expelling elements 1 and 2 for coordinated reciprocation. This drive means in the illustrated embodiment of FIGS. 1–3 has a crank 9, a crank rod 10 and a crosshead piston 11 which drive the expelling element 1, and a rack drive 12 which drives the expelling element 2 with which it is connected, and which receives motion from the crank 9. The crosshead piston 11 is centrically connected with the trailing end $1^{IV}$ of the expelling element 1 and is guided in a sleeve 11'. The crank 9 is configurated as a flat bevel gear 9 which projects beyond the travel path 9' of a crank rod pin 9". This gear 9 meshes with a bevel pinion 13 whose axis 13' is aligned with the axis of the crosshead piston 11 and that of the expelling element 1; at the rear end 13" of the axis 13', which projects out of the appliance, a known socket coupling 14 is provided, and between the coupling 14 and the end 13' a slip clutch 15 is arranged.

The axis of rotation 9''' of the gear 9 is located in the plane of symmetry of the appliance. The rack drive 12 utilizes a projection 16 resembling a segment of a circle and provided on the underside of the gear 9, and a rack 17 which is of circular cross section and arranged below the axis 13' of the pinion 13. During each complete 360° revolution of the gear 9 the projection 16 moves once into engagement with the teeth 17' of the rack 17 and advances the latter by a distance corresponding to the spacing $t_z$ between consecutive teeth, so that the projection 16 during each following 360° revolution again engages with the next-following tooth of the rack 17. The distance $t_z$ corresponds approximately to the diameter $d$ of the sleeve portion $4^{IV}$. This assures that during each complete revolution of the gear 9 only so much of the filler material can be expelled from the magazine outlet 3''' into the discharge nipple 4 via the projection 16, the teeth 17' and the expelling element 2, as can be accommodated in the discharge nipple 4. The length L of the set of teeth 17' is equal to the length of the maximum advancement of which the expelling element 2 is capable until it reaches the outlet 3''' of the magazine 3, so that the leading end of the expelling element 2 cannot enter into the sleeve portion $4^{IV}$ and interfere in any way with the expulsion of material from the discharge nipple 4 into a tooth cavity.

The device in FIGS. 1–3 operates as follows:

The coupling 14 is connected with a source of motive power, for example with the output shaft of an electric motor. Thereupon, the pinion 13 is rotated via the slip coupling 15 and the shaft 13', and in turn drives the gear 9. At this time, the crosshead piston 11 and therefore the expelling element 1 are to be in the rearward end position of the crank rod 10 as illustrated in FIG. 1. In this position the leading end 1''' of the expelling element 1 is located just short of the communication between the opening 3''' of the magazine 3 with the interior channel of the nipple 4. During the subsequently following 180° revolution of the gear 9 the crosshead piston 11 is shifted to its forward end position, whereas at the same time the forward end portion 1''' of the expelling element 1 moves to the outlet $4^V$ of the sleeve portion $4^{IV}$. In this forward end position of the crank rod 10 the forward end portion 1''' of the expelling element 1 blocks the outlet $4^V$ whereas at the same time the trailing 11'' of the crosshead piston 11 is engaged by an arresting member 18' that can be released via a slider 19 counter to the force of the spring 18. This prevents the crosshead piston 11 and therefore the expelling element 1 from moving rearwardly, so that in this position in which the outlet $4^V$ is blocked, the sleeve portion $4^{IV}$ can be used as a compactor for compacting the filler material that has just been introduced into a tooth cavity. However, during the respective introduction of material into a tooth cavity, the member 19 is pushed back and therefore the member 18' is depressed against the force of the spring 18, so that the crosshead piston 11 can slide rearwardly without hindrance.

In the vicinity of the rear end position of the crank rod 10 and the crosshead piston 11 the projection 16 moves into engagement with the next tooth 17'' of the teeth 17', to push the rack 17 forwardly by the distance $t_z$ until the projection 16 becomes disengaged from the teeth 17'. This advancement of the rack 17 causes the expelling element 2 also to be advanced, so that the filler material accommodated in the interior of the magazine 3 is advanced by a similar distance, equal to the diameter $d$ in the interior of the nipple 4. For reasons of clarity the distance $t_z$ has been shown greater than the diameter $d$ in the drawing, although they are actually identical. After a quantity of filler material corresponding in length to the dimensions $d = t_z$ has been pushed into the interior channel of the discharge nipple 4, the working stroke of the expelling element 1 begins. During the continued turning of the gear 9 motion is transmitted via the crank rod 10 and the crosshead piston 11 so that the expelling element 1 is advanced and its forward end portion 1''' squeezes off the portion of filler material that has entered the interior channel of the discharge nipple 4, at the magazine outlet opening 3''', and pushes it out of the outlet $4^V$ and into the tooth cavity into registry with which the outlet has been placed. This operation is continued during each revolution of the gear 9 until the rack 17 has moved its forward end position and the magazine 3 is completely emptied of filler material. In this forward end position of the rack 17 the projection 16 is located in the forward end position of the crank rod 10 ahead of the rack 17, so that the rack can be pushed back into its rearward end position via a pin $17^{IV}$ that is guided in a longitudinal slot 17'''' in the housing of the device. Thereafter the empty magazine 3 can be rapidly placed by a previously filled magazine 3 and operations can continue.

While the sleeve portion $4^{IV}$ is utilized for compacting the quantity of filler material that has just been introduced into the cavity, the member 19 is pushed forward so that the member 18' can engage behind the rear edge 11'' of the crosshead piston 11 under the urging of the spring 18, to thereby block the gear 9 and the pinion 17 from further rotation. In this operating condition the clutch 15 slips so that the electric drive which is connected with the coupling 14 can continue to turn without becoming damaged.

To assure proper and reliable operation of the appliance according to the present invention it is important that when the crank rod 10 is in its rear end position the projection 16 is disengaged from the teeth 17' and the forward end 1''' of the expelling element 1 is spaced from the upper outlet edge $3^V$ of the magazine 3 by a distance $t_m$ which is equal to the difference between the radius $r$ of the mean circular path of the projection 16 and the normal spacing $a$ of the axis of rotation 9''' to the secant $s$ of this means path of rotation intermediate the point of engagement $17^V$ and disengagement $17^{VI}$ of the projection 16 with the teeth 17'. This assures that the forward end 1''' of the expelling element 1 begins the working stroke and moves towards the outlet $4^V$ of the discharge nipple 4 only when the expelling element 2 has expelled a quantity of filler material from the magazine 3 into the discharge nipple 4 corresponding to the spacing $t_z$, that is only after the charging of the material into the nipple 4 is completed Whereas FIGS. 1–3 illustrates an embodiment of the invention wherein a mechanical drive is used, FIGS. 4–7 and 8–10 illustrate two embodiments of the invention wherein pneumatic drives are used which couple the expelling elements 1 and 2 with one another. The pneumatic drives utilize at least one manual control valve 20 and two double-acting circular pistons 21 and 22 of which the piston 21 is connected with the rear end $1^{IV}$ of the expelling element 1 and the piston 22 is similarly connected with the rear end 2'' of the expelling element 2. The manual control valve 20 can be operated against the force of a biasing spring 23 and is subdivided by three sealing rings 20'''' on the valve shaft into an upper annular compartment 20' and a lower annular compartment 20'' which are airtightly separated from one another. In the vicinity of the upper sealing ring and the lower sealing ring 20''' the valve wall is formed with respective vent openings $20^{IV}$ and $20^V$ via which the upper and lower annular compartment 20' and 20''' can be vented. The pistons 21 and 22 are located in the symmetry plane of the respective appliance and are accommodated in sleeves 21' and 22' which have identical diameters.

Figure 4:
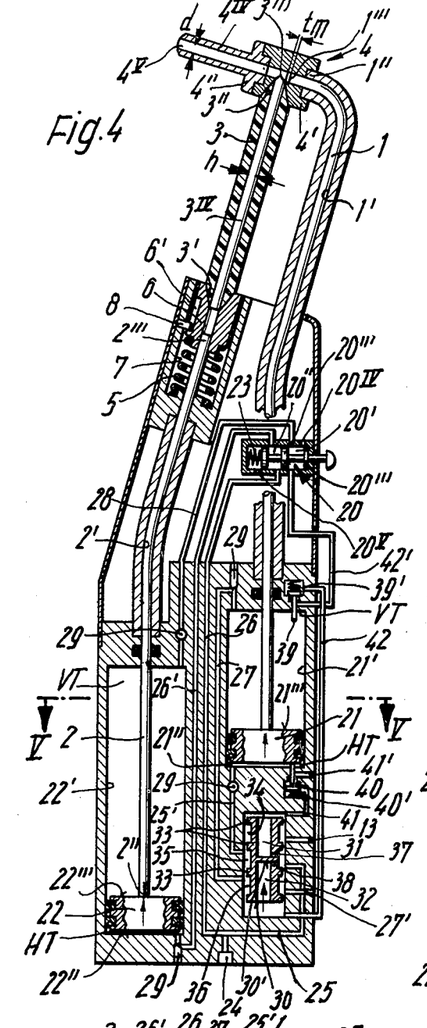
FIG. 4 is a view similar to FIG. 1, but illustrating a further embodiment of the invention having a pneumatic drive means.
Figure 5:
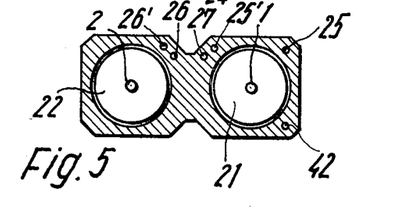
FIG. 5 is a section taken on line V—V of FIG. 4.
Figure 6:
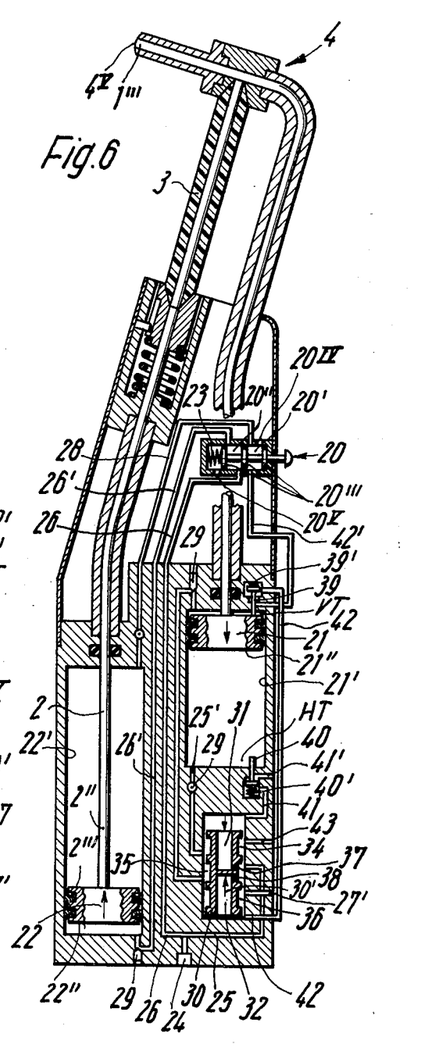
FIG. 6 is a view similar to FIG. 4, but illustrating the device of FIG. 4 in a different operating position.
Figure 7:
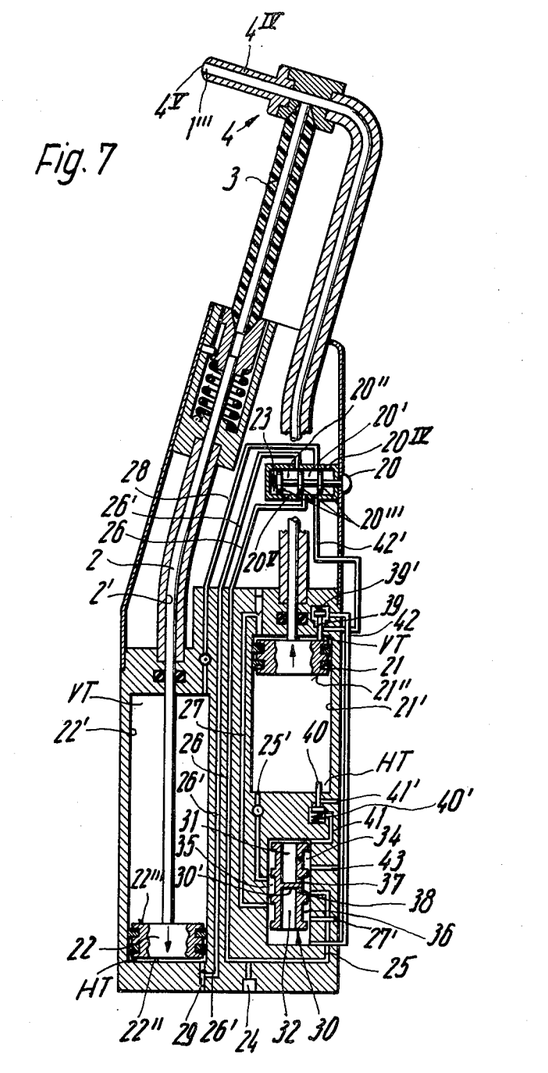
FIG. 7 is another view similar to FIG. 4, illustrating the device in still a further operating position.
Figure 8:
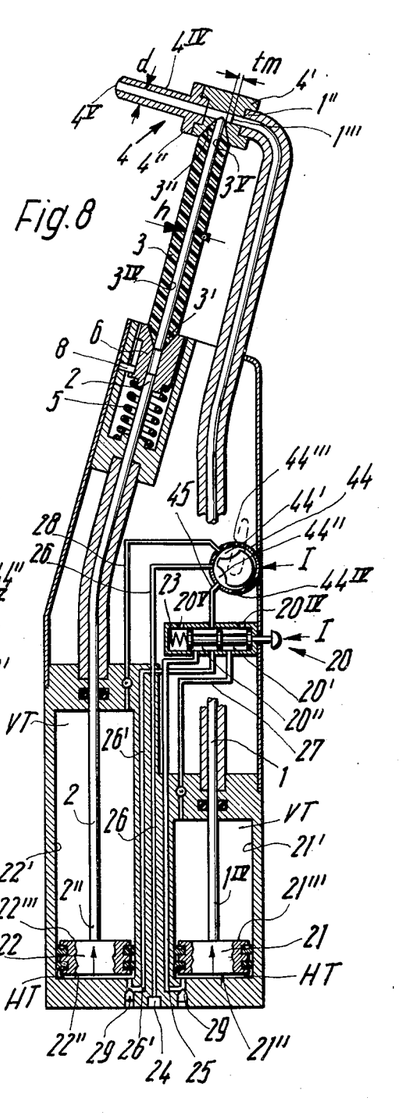
FIG. 8 is a view similar to FIG. 1, illustrating an additional embodiment of the invention, which is a modification of the embodiment in FIG. 4.
Figure 9:
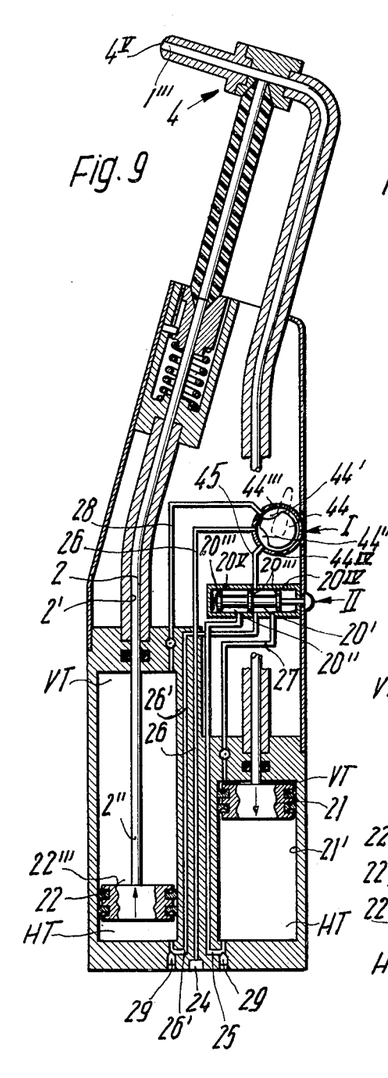
FIG. 9 is a view similar to FIG. 8, illustrating the device of FIG. 8 in a different operating position.
Figure 10:
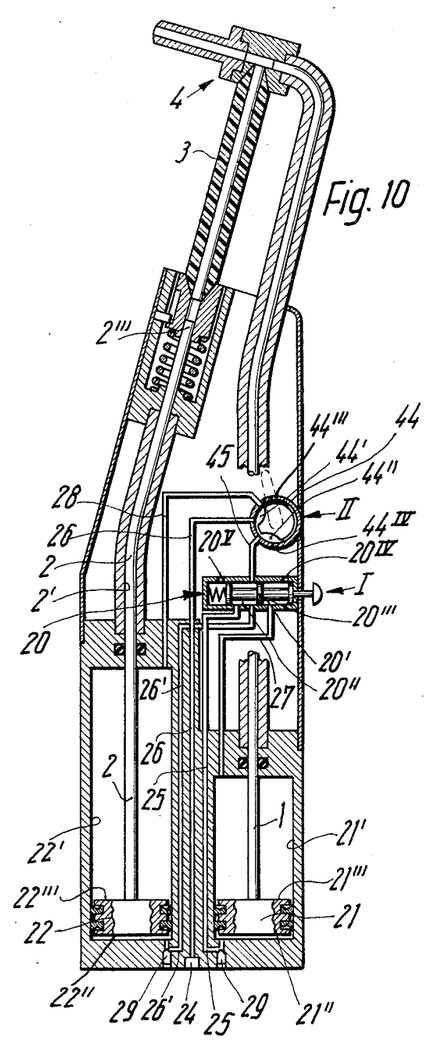
FIG. 10 is a view similar to FIG. 8, illustrating the device of that Figure in still a further operating position.

When the expelling element 21 is in its forward end position VT the front end 1''' of the element 1 blocks the outlet $4^V$ of the discharge nipple 4, as shown in FIGS. 6, 7 and 9. When the element 1 is in its rearward end position HT, the front end 1''' is retracted from but located adjacent of the opening 3''' of the magazine 3, as shown in FIGS. 4, 8 and 10.

Provided at the rear end of the respective appliance is a central air supply inlet conduit 24. FIGS. 4, 6 and 7 show the conduit 24 to be connected via supply lines 25 and 25' with the working side 21'' of the piston 21, and also to be connected via supply lines 26, the valve 20 and a supply line 26' with the working side 22'' of the piston 22. At the piston rod or retracting side 21''' of the piston 21, at the rear end of the sleeve 21, I have provided a retracting line 27; a similar retracting line 28 is provided at the piston rod or retracting side 22''' of the piston 22, at the rear end of the sleeve 22'. The cross sections of the lines 25, 25' and 26, 26' and of the lines 27, 28 can be varied by adjustable pins 29, so that the flow of air can be throttled and the pressure in the individual lines and thereby the operating speed of the piston 21 and 22 can be regulated.

In the embodiment of FIGS. 4–7 the central air supply conduit 24 is connected via the lines 26, 26' of the piston 22 with the valve 20, and via lines 25, 25' with an air piston valve 30. The lines 25, 25' and 27 of the piston 21 communicate with the valve 30 and the advancing and retracting lines 26, 26' and 28 of the piston 22 communicate with the valve 20.

The valve 30 comprises a hollow cylinder which is horizontally mounted in the appliance and is subdivided in its interior by a partition 30' into two chambers 31 and 32. At its outer side it is subdivided by four sealing rings 33 into three annular chambers 34, 35 and 36. The center chamber 35 is always in communication with the conduit 24 via the line 25, and it is further in communication with the chambers 31 and 32 via two openings 37 and 38, respectively. At the piston rod side 21''' and at the working side 21'' of the piston 21 the cylinder or sleeve 21' is each provided with a respective reversing valve 39, 40 which can be opened by engagement with the piston 21 counter to the force of a respective spring 39', 40', to reverse the direction of movement of the piston 21.

The embodiment illustrated in FIGS. 4–7 operates as follows:

In the working phase shown in FIG. 4 the piston 21 engages the reversing valve 40, whereas the valve 30 is in its forward position and the valve 20 is maintained in raised position by the spring 23. In this working phase air is supplied via the conduit 24, the line 25 and the center chamber 35 through the opening 37 into the upper chamber 31 and through the opening 38 into the lower chamber 32. Since the valve 40 is moved to open position by engagement with the piston 21, counter to the force of the spring 40', the upper chamber 31 is vented via the lines 41, 41'. Since at the same time the full air pressure acts upon the surface area of the partition 30' in the chamber 32, the valve 30 is maintained immovably in the position illustrated in FIG. 4 even when vibrations are transmitted to the appliance. At the same time the interior of the sleeve 21' at the piston rod side 21''' is vented via the line 27, the chamber 36 and the line 27'. Due to this arrangement the piston 21' is shifted in the direction indicated by the arrow towards the reversing valve 39. During the entire stroke of the piston 21 the piston 22 is subjected to air pressure at its working side 22'' via the line 26, the chamber 20'' and the line 26, whereas at the piston rod side 22''' the interior of the sleeve 22' is vented via the line 28, the chamber 20' and the vent opening 20$^{IV}$ in the wall of the valve 20. As a result of this, the piston 22 shifts the expelling element 2 in direction towards the discharge nipple 4, so that a preselected quantity of the filler material accommodated in the magazine 3 is pressed into the nipple 4, where it is squeezed off by the expelling element 1 and expelled through the outlet 4$^V$ into the tooth cavity to be filled.

In this operating phase the piston 21 has assumed the position shown in FIG. 6 and has operated the reversing valve 39. As a result, the chamber 32 of the valve 30 is now connected with the chamber 20' of the valve 20 via the lines 42, 42', and is vented via the vent opening 20$^{IV}$ in the wall of the valve 20. Since at the same time the reversing valve 40 at the opposite side of the piston is closed, air at full pressure is admitted via the conduit 24, the line 25, the chamber 35 and the opening 37 into the chamber 31, so that the full surface area of the partition 30' is subjected to air pressure and the valve 30 is moved to the position illustrated in FIG. 6. In this position the interior of the sleeve 21' located at the working side 21'' of the piston 21 is vented via the line 25', the chamber 34 and the line 43, whereas at the same time the conduit 24 is placed in communication with the piston rod side 21''' of the piston 21 via the conduit 25, the chamber 35 and the line 27. As a result of this the piston 33 reverses its direction of movement and now again moves towards the valve 40. These direction reversals continue, and during the operation of the piston 21 in this manner the piston 22 is always subjected in the previously described manner at its working side 22'' by air from the conduit 24, and vented at its piston rod side 22'''. Therefore, prior to each beginning working stroke of the expelling element 1 the requisite quantity of filler material is expelled by the expelling element 2 from the magazine 3 into the nipple 4. The constantly reciprocating movement of the piston 21 always alternately operates the valve 39 and the valve 40, so that the valve 30 alternately and automatically moves into the piston of FIG. 4 into the position of FIG. 6. Thus, during each working stroke of the piston 21 small partial quantities of filler material are expelled in rapid succession from the magazine 3 into the discharge nipple 4, and from there into the tooth cavity.

In order to be able to use the appliance not only for filling of the cavity, but at any time also for compacting of the admitted filler material, the filling operation can be immediately interrupted whenever desired, by depressing the manual control valve 20. This working phase of the appliance is illustrated in FIG. 7 where it will be seen that depressing of the valve 20 counter to the force of the spring 23 connects the chamber 20'' with the vent opening 20$^V$, and at the same time the chamber 20' of the valve 20 is closed off from the vent opening 20$^{IV}$ by the sealing ring 20'''. As a result of this, the valve 30 is now uniformly subjected to constant air pressure at opposite sides of its partition 30' in the two chambers 31 and 32, since on the one hand air travels from the conduit 24 via the line 25 and the chamber 35 and through the openings 37 and 38 into the two chambers 31 and 32. The air cannot excape from the chamber 31 since the valve 40 is closed. From the chamber 32 the air also cannot escape because this chamber 32 is now connected via the lines 42, 42' (since the valve 39 is opened) with the chamber 20' of the valve 20. This chamber 20' is separated from the vent opening 20$^{IV}$ and therefore is under the influence of the pressure acting in the central air supply conduit 24, via the line 26 which communicates with the chamber 20'. Since the line 28 of the piston 22 also communicates with the chamber 20'. the piston 22 is returned into the position shown in FIG. 7, because the working side 22' of the piston 22 is also connected with the chamber 20' of the valve 20 via the line 26'. The chamber 20'' of the valve 20 is vented via the vent opening 20$^V$, and the piston rod side 21''' of the piston 21 is also vented via the line 27, the chamber 36 and the line 27'. At the same time the piston 21 is subjected to air pressure from the conduit 24 which acts via the line 25, the chamber 35 and the line 25' upon the working side 21″, to maintain the piston 21 in the position shown in FIG. 7 in which the forward end 1‴ of the expelling element 1 blocks the outlet 4$^V$ of the discharge nipple 4, so that the sleeve portion 4$^{IV}$ can be used as a compacting and tamping element to compact the quantity of filler material previously admitted into a tooth cavity. To continue the filling operation it is merely necessary to release the manual control valve 20, which is then restored to the position shown in FIGS. 4 and 6 by the spring 23, so that the filling operation continues in the manner and at the speed described above.

The embodiment in FIGS. 8–10 is analogous to that of FIGS. 4–7, but constitutes a simplified form thereof. The embodiment of FIGS. 8–10 again has the valve 20, but in addition has a manually controlled reversing valve 44 for reversing the movements of the piston 22. It does not have the valve 30. The central air supply conduit 24 is connected via the line 26 with the valve 44 which in the illustrated embodiment is constructed as a circular piston valve having two valve chambers 44′ and 44″ as well as two vent openings 44‴ and 44$^{IV}$. The reversing line 28 of the piston 22 communicates with the valve chamber 44′ and is always vented via the opening 44‴ during the filling of a tooth cavity. The central line 26 and a connecting line 45 to the valve 20 always communicate with the chamber 44″ during the filling of a tooth cavity, that is during the time during which the expelling element 1 expels material from the nipple 4.

The valve 20 is again operable counter to the spring 23, as in the preceding embodiment, and is provided on its valve shaft with three sealing rings 20‴ which fluid-tightly separate two annular chambers 20′ and 20″ from one another. In the region of the upper sealing ring 20‴ there is provided a vent opening 20$^{IV}$ and a similar vent opening 20$^V$ is provided in the region of the lower sealing ring 20‴. The advancing line 25 for the piston 21 and the advancing line 26′ for the piston 22 both communicate with the annular chamber 20″. The annular chamber 20′ of the valve 20 is connncted with the restoring line 27 of the piston 21.

The embodiment in FIGS. 8–10 operates as follows:

The valve 20 and the valve 44 each have two operating positions I and II. In FIG. 8 the valve 44 and the valve 20 are each in the respective valve position I, and in this operating phase air is admitted via the central air supply conduit 24 and the line 26 into the valve chamber 44″, and therefore into the line 45 and the chamber 20″. The working side 22′ of the piston 22 therefore receives pressure fluid via the line 26′, and the working side 21″ of the piston 21 also receives pressure fluid via the line 25. At the same time, the piston rod side 22‴ of the piston 22 is vented via the line 28, the valve chamber 44′ and the vent opening 44‴. The piston rod side 21‴ of the piston 21 is also vented via the line 27, the annular chamber 20′ and the vent opening 20$^{IV}$. This operating phase is shown in FIG. 8, and in it the piston 21 and the piston 22 move in the directions indicated by the arrows, so that the expelling element 2 pushes a quntity of filler material out of the magazine 3 into the nipple 4, where it is expelled from the nipple 4 through the outlet 4$^V$ by the expelling element 1, into the cavity on which work is being performed.

At the end of the working stroke of the piston 21 the direction of movement of the same must be reversed. For this purpose the valve 20 must be manually depressed to assume the second position II shown in FIG. 9, whereas the valve 44 remains in its position I. The piston 22 continues to receive pressurized air from the conduit 24 via the line 26′, the chamber 20′, the line 45, the valve chamber 44′ and the line 26; the chamber 20″ is however now vented via the open end 20$^V$, so that the line 25 of the piston 21 is also vented. At the same time the line 27 is connected via the chamber 20′ which is separated from the vent opening 20$^{IV}$ and now communicates with the line 45, the valve chamber 44″ and the line 26, so that the piston 21 now moves in the opposite direction as indicated by the arrow in FIG. 9. Alternating depressing and releasing of the valve 20 therefore causes the piston 21 to move alternately to the position shown in FIGS. 8 and 9, so that a complete forward and reversal movement of the piston 21 corresponds to a complete filling cycle, that is the admission of material into the nipple 4 and its expulsion from the same into a tooth cavity. If the valve 20 is depressed and retained in the position II shown in FIG. 9, then the expelling member 1 moves to its forward end position, in which its front end 1‴ blocks the outlet 4$^V$ so that the nipple 4 can now be used to tamp and condense the material that has already been admitted into the tooth cavity.

When the filler material accommodated in the magazine 3 has all been expelled, the magazine must be replaced with a new one. For this purpose, the expelling element 2 and the piston 22 must be retracted. This is accomplished in that the valve 44 is switched to the position II shown in FIG. 10, and during this operation the valve 20 may either be allowed to remain in the position I but can also be moved into its position II, as desired. When the valve 44 assumes its position II as shown in FIG 10, the air supply conduit 24 is connected with the valve chamber 44′ via the line 26, and the valve chamber 44′ is now disconnected from the vent opening 44‴ and supplies compressed air via the line 28 to the piston rod 22‴ of the piston 20. At the same time the working side 22″ of the piston 22 is vented via the line 26′. When the valve 20 is in its position I (as shown in FIG. 10) this venting takes place via the chamber 20″, the line 45, the chamber 44″ and the vent opening 44$^{IV}$. If the valve 20 should happen to be in its position II, as shown in FIG. 9, then the line 26′ of the piston 22 would be placed into communication with the line 45 via the chamber 20′, and would then be vented via the chamber 44″ and the vent opening 44$^{IV}$.

As soon as the piston 22 has been retracted to the position shown in FIG. 10, the magazine 3 can be removed and replaced with a filled one in the amnner described earlier. It is important that the stroke length of the piston 22 is so selected that the forward end 2‴ of the expelling element 2 is so far retracted from the inlet opening into the magazine 3 that the latter can be pushed downwardly together with the member 6 against the force of the spring 5, without running the risk that the forward end 2‴ might again enter into the magazine 3.

It will be appreciated that only exemplary embodiments of the invention have been illustrated for purpose of explanation, and that various modifications may be made in these embodiments without departing in any way from the intent and concept of the invention.

It will be understood that each of the elements described above, or two or more together, may also find a useful application in other types of constructions differing from the types described above.

While the invention has been illustrated and described as embodied in a dental appliance, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A dental appliance for introducing a filler material into a tooth cavity, comprising a support; a discharge nipple on said support and having an elongated interior channel formed with an inlet and an outlet; first means forming a first passage having an open end; second means forming a second passage which communicates with said inlet; a replaceable magazine on said support and having an elongated chamber for a quantity of said filler material, said chamber communicating with said open end and with said channel in direction transverse to the elongation of the channel; a first expelling element reciprocable in said first passage and chamber for expelling a portion of said filler material and charging it into said channel; a second expelling element reciprocable in said second passage and channel for expelling said portion through said outlet; a single drive means for effecting coordinated reciprocation of both of said expelling elements and comprising a pair of double-acting pistons, each for a respective one of said expelling members and each having a working side and a retracting side, centrally located air supply means at a rear end of said appliance, first conduit means connecting said air supply means with said working sides, and second conduit means connecting said air supply means with said retracting sides of said pistons; an air valve connected with the first and second conduit means of the piston for said second expelling element and comprising a hollow cylinder horizontally mounted in said appliance, a partition dividing the interior of said cylinder in two compartments, and sealing rings forming with said cylinder three axially successive annular chambers a center one of which permanently communicates with said air supply and has two apertures each of which communicates with one of said compartments; a manual control valve connected with the first and second conduit means of the piston for said first expelling element; and a pair of connecting conduits connecting said air supply with said air valve and said manual control valve, respectively.

2. A dental appliance as defined in claim 1; further comprising a pair of spring-loaded reversing valves interposed in said conduit means and respectively located at said working side and retracting side of the piston for said second expelling element and operable by engagement with said piston so as to reverse the direction of movement thereof.

3. A dental appliance as defined in claim 2, wherein the one reversing valve at said working side of said piston for said second expelling element vents one of said two compartments when operated by engagement with said piston, and terminates venting of said one compartment when said one reversing valve is disengaged by said piston while simultaneously the working side of said piston for said second expelling element receives air from said center annular chamber and the retracting side of said piston for said second expelling element is vented via another one of said annular chambers.

4. A dental appliance as defined in claim 2, wherein the one reversing valve at the retracting side of said piston for said second expelling element vents, when operated by engagement with said piston, one of said compartments via conduit means leading to said manual control valve and a venting opening of the latter, and when disengaged by said piston terminates venting of said one compartment while at the same time said air valve moves to a position in which said second conduit means of said piston receives air via said center annular chamber and said working side of said piston is vented.

5. A dental appliance as defined in claim 4, wherein operation of said manual control valve serves to retain said piston for said second expelling element in a position in which it engages said one reversing valve and in which said one compartment is connected with said first conduit means of the piston for said first expelling element, while at the same time said second conduit means of said piston for said first expelling element receives air and said first conduit means of said piston for said first expelling element is vented.

6. A dental appliance for introducing a filler material into a tooth cavity, comprising a support; a discharge nipple on said support and having an elongated interior channel formed with an inlet and an outlet; first means forming a first passage having an open end; second means forming a second passage which communicates with said inlet; a replaceable magazine on said support and having an elongated chamber for a quantity of said filler material, said chamber communicating with said open end and with said channel in direction transverse to the elongation of the channel; a first expelling element reciprocable in said first passage and chamber for expelling a portion of said filler material and charging it into said channel; a second expelling element reciprocable in said second passage and channel for expelling said portion through said outlet; and a single drive means for effecting coordinated reciprocation of both of said expelling elements and comprising a pair of double-acting pistons, each for a respective one of said expelling members and each hving a working side and a retracting side, centrally located air supply means at a rear end of said appliance, first conduit means connecting said air supply means with said working sides, and second conduit means connecting said air supply means with said retracting sides of said pistons, and a manually operable reversing valve for the piston for said first expelling element, said reversing valve being connected with said air supply, with said second conduit means of said piston for said first expelling element, and with a connecting conduit which communicates with a manual control valve to which said first conduit means of said piston for said first expelling element and said first and second conduit means of said piston for second expelling element are connected.

7. A dental appliance as defined in claim 6; further comprising a pair of vent openings in said reversing valve in the regions where said second conduit means of the piston for said first expelling element and said connecting conduit communicate with said reversing valve.

8. A dental appliance as defined in claim 7, wherein said reversing valve is movable between a first operating position in which said connecting conduit is connected to said air supply and said second conduit means of the piston for said first expelling means is vented via one of said vent openings, and a second operating position in which said second conduit means of the piston for said first expelling means is connected to said air supply and said connecting conduit means is vented via the other of said vent openings.

9. A dental appliance as defined in claim 8, wherein said manual control valve has a first control position and a second control position in each of which said connecting conduit communicates with said first conduit means of the piston for said first expelling element.

10. A dental appliance as defined in claim 9, wherein said second conduit means of the piston for said second expelling element is vented via one of said vent openings, and said first conduit means of said pistons for said expelling elements are connected to said air supply, when said manual control valve is in said first control position and said reversing valve is in said second operating position.

11. A dental appliance as defined in claim 9, wherein said first conduit means of the piston for said second expelling means is vented via one of said vent openings, whereas said second conduit means of the piston for said second expelling means and said first conduit means of the piston for said first expelling means are connected to said air supply via said manual control valve, when said manual control valve is in said second control position while at the same time said reversing valve is in said first operating position.

12. A dental appliance for introducing a filler material into a tooth cavity, said applicance comprising: an elongated support; a discharge nipple at one end of said support having an elongated interior channel formed with an outlet opening transversely to said support, an inlet opening longitudinally of said support, and a lateral opening intermediate said inlet and said outlet and itself opening longitudinally of said support; means in said support forming a passage having an open end directed generally longitudinally of said support toward said nipple and in line with said lateral opening; a replaceable magazine engageable between said open end and said lateral opening and having a throughgoing chamber adapted to hold a body of said material and open to said open end and to said lateral opening; a first expelling element reciprocal through said passage and said chamber; a first piston carried on said first element; a first cylinder in said housing surrounding said first piston and subdivided thereby into a front compartment and a rear compartment; first valve means effective in a first position for feeding air under pressure into said rear compartment and thereby advancing said first element through said chamber to push material therein into said channel through said lateral opening and effective in a second position to withdraw said element from said chamber into said passage; a second expelling element formed as a flexible wire having a tip reciprocal in said passage past said lateral opening; a second piston carried on said second element; a second cylinder in said housing surrounding said second piston and subdivided thereby into a front compartment and a rear compartment; and second valve means effective in one position for supplying air under pressure to said rear compartment of said second cylinder to push said tip in said channel past said lateral opening toward said outlet and effective in another position for withdrawing said tip away from said outlet past said lateral opening.

13. The appliance defined in claim 12, further comprising reversing means connected to said second valve means for automatically and periodically switching same between said one position and said other position.

14. A dental appliance as defined in claim 12, wherein said second expelling element is movable between a forward end position in which said tip blocks said outlet of said channel and a rearward end position in which said tip is located in said channel intermediate said lateral opening and said inlet.

15. A dental appliance as defined in claim 12, said valve means comprising centrally located air supply means at a rear end of said appliance, first conduit means connecting said air supply means with said working sides and second conduit means connecting said air supply means with said retracting sides of said pistons.

16. A dental appliance as defined in claim 15; and further comprising adjustable throttling pins for varying the cross-sections of said first and second conduit means to thereby throttle the flow of air therethrough.

17. A dental appliance as defined in claim 15; said valve means further comprising an air valve connected with the first and second conduit means of said second piston; a manual control valve connected with the first and second conduit means of said first piston; and a pair of connecting conduits connecting said air supply with said air valves and said manual control valve, respectively.

18. A dental appliance as defined in claim 17, said air valve comprising a hollow cylinder horizontally mounted in said appliance, a partition dividing the interior of said cylinder in two compartments, and sealing rings forming with said cylinder three axially successive annular chambers a center one of which permanently communicates with said air supply and has two apertures each of which communicates with one of said compartments.

19. A dental appliance as defined in claim 18, wherein said second valve means comprises a pair of spring-loaded reversing valves interposed in said conduit means and located at opposite sides of said second piston and operable by engagement therewith to reverse the direction of movement thereof.

20. A dental appliance as defined in claim 19, wherein the one reversing valve at one side of said second piston vents the respective compartment when operated by engagement with said second piston, and terminates venting of the respective compartment when said one reversing valve is disengaged by said piston while simultaneously the other side of said second piston receives air and the other side of said second piston is vented.

21. A dental appliance as defined in claim 19, wherein the one reversing valve at one side of said second piston vents when operated by engagement with said second piston the respective compartment via conduit means leading to said manual control valve and a venting opening of the latter, and when disengaged by said second piston terminates venting of the respective compartment while at the same time said air valve means moves to a position in which said second conduit means of said second piston receives air and the other side of said second piston is vented.

22. A dental appliance as defined in claim 21, wherein operation of said manual control valve serves to retain said second piston in a position in which it engages said one reversing valve and in which the respective compartment is connected with said first conduit means of said first piston while at the same time said second conduit means of said first piston receives air and said first conduit means of said first piston is vented.

23. A dental appliance as defined in claim 15; further comprising a manually operable reversing valve for said first piston, said reversing valve being connected with said air supply, with said second conduit means of said first piston, and with a connecting conduit which communicates with a manual control valve to which said first conduit means of said first piston and said first and second conduit means of said second piston are connected.

24. A dental appliance as defined in claim 23 further comprising a pair of vent openings in said reversing valve in the regions where said second conduit means of said first piston and said connecting conduit communicate with said reversing valve.

25. A dental appliance as defined in claim 24, wherein said reversing valve is movable between a first operating position in which said connecting conduit is connected to said air supply and said second conduit means of said first piston is vented via one of said vent openings, and a second operating position in which said second conduit means of said first piston is connected to said air supply and said connecting conduit means is vented via the other of said vent openings.

26. A dental appliance as defined in claim 15, wherein said manual control valve has a first control position and a second control position in each of which said connecting conduit communicates with said first conduit means of said first piston.

27. A dental appliance as defined in claim 21, wherein said second conduit means of said second piston is vented via one of said vent openings, and said first conduit means of said pistons are connected to said air supply when said manual control valve is in said first control position and said reversing valve is in said second operating position.

28. A dental appliance as defined in claim 26 wherein said first conduit means of said second piston is vented via one of said vent openings, whereas said second conduit means of said second piston and said first conduit means of said first piston are connected to said air supply via said manual control valve, when said manual control valve is in said second control position while at the same time said reversing valve is in said first operating position.

29. A dental appliance as defined in claim 12, wherein said magazine is a sleeve having conically tapering end portions.

30. A dental appliance as defined in claim 29, wherein one of said end portions faces away from said nipple and engages a spring-biased retaining member which is mounted coaxially relative to said first means.

31. A dental appliance as defined in claim 12, wherein said nipple comprises a first sleeve part fixedly connected with said housing at said open end, and a second sleeve portion releasably connected with said first sleeve portion and projecting axially thereof.

32. A dental applicance as defined in claim 12, wherein said expelling elements are flexible, corrosion-resistant wires of metallic material, each received over at least a substantial part of its length in the respective passage and channel.

33. A dental appliance as defined in claim 12, wherein said expelling elements are flexible, corrosion-resistant wires of synthetic plastic material, each received over at least a substantial part of its length in the respective passage and channel.

34. A dental appliance as defined in claim 33, wherein said synthetic plastic material is tetrafluoroethylene.

* * * * *